United States Patent [19]

Jinoian et al.

[11] Patent Number: 4,957,435

[45] Date of Patent: Sep. 18, 1990

[54] DENTAL LABORATORY DIE TRAY

[75] Inventors: Vanik N. Jinoian, Obermumph, Switzerland; Ray E. Morrow; Wayne W. Whitehill, both of Arcadia, Calif.

[73] Assignee: Vident, Inc., Baldwin Park, Calif.

[21] Appl. No.: 254,441

[22] Filed: Oct. 6, 1988

[51] Int. Cl.$^5$ .............................................. A61C 19/00
[52] U.S. Cl. ..................................... 433/34; 425/175; 425/179; 425/180
[58] Field of Search ............................. 433/34, 36, 74; 425/175, 176, 179, 180; 264/16; 249/54, 82

[56] References Cited

U.S. PATENT DOCUMENTS

| | | | |
|---|---|---|---|
| 2,274,186 | 2/1942 | Brace | 164/65 |
| 2,368,721 | 2/1945 | Moskey | 249/54 |
| 2,574,593 | 11/1951 | Scharfe | 425/180 |
| 2,678,469 | 5/1954 | Dimmer | 525/198 |
| 3,182,358 | 5/1965 | Van Rossem | 249/54 |
| 3,210,444 | 10/1965 | Schwarz | 264/16 |
| 3,224,044 | 12/1965 | Harris | 425/180 |
| 3,332,658 | 7/1967 | Lemelson | 249/139 |
| 3,543,303 | 11/1970 | Sacchiero | 249/164 |
| 4,161,067 | 7/1979 | Bekey et al. | 433/42 |
| 4,182,507 | 1/1980 | Bekey et al. | 249/128 |

FOREIGN PATENT DOCUMENTS 2092058  8/1982  United Kingdom ................ 425/175

OTHER PUBLICATIONS

Vol. 10, Jun. 1986, Quintessence of Dental Technology, cover page and pp. 324 and 454.
Whaledent International Accu-Trac brochure, two pages.
Di-Equi Dental Products brochure, six sheets.

*Primary Examiner*—Cary E. Stone
*Attorney, Agent, or Firm*—Harris, Kern, Wallen & Tinsley

[57] ABSTRACT

A dental laboratory die tray having first and second side members and a bottom member with the side members being joinable to form a housing with an open top and an open bottom, and with the bottom member being holdable between to the side members to close the open bottom when the side members are in a housing closed position. The side members may be moved away from each other to a partially closed position permitting removal and reinsertion of the bottom member, thereby providing a die tray with a closed bottom for some operations and with an open bottom for other operations.

11 Claims, 1 Drawing Sheet

U.S. Patent
Sep. 18, 1990
4,957,435
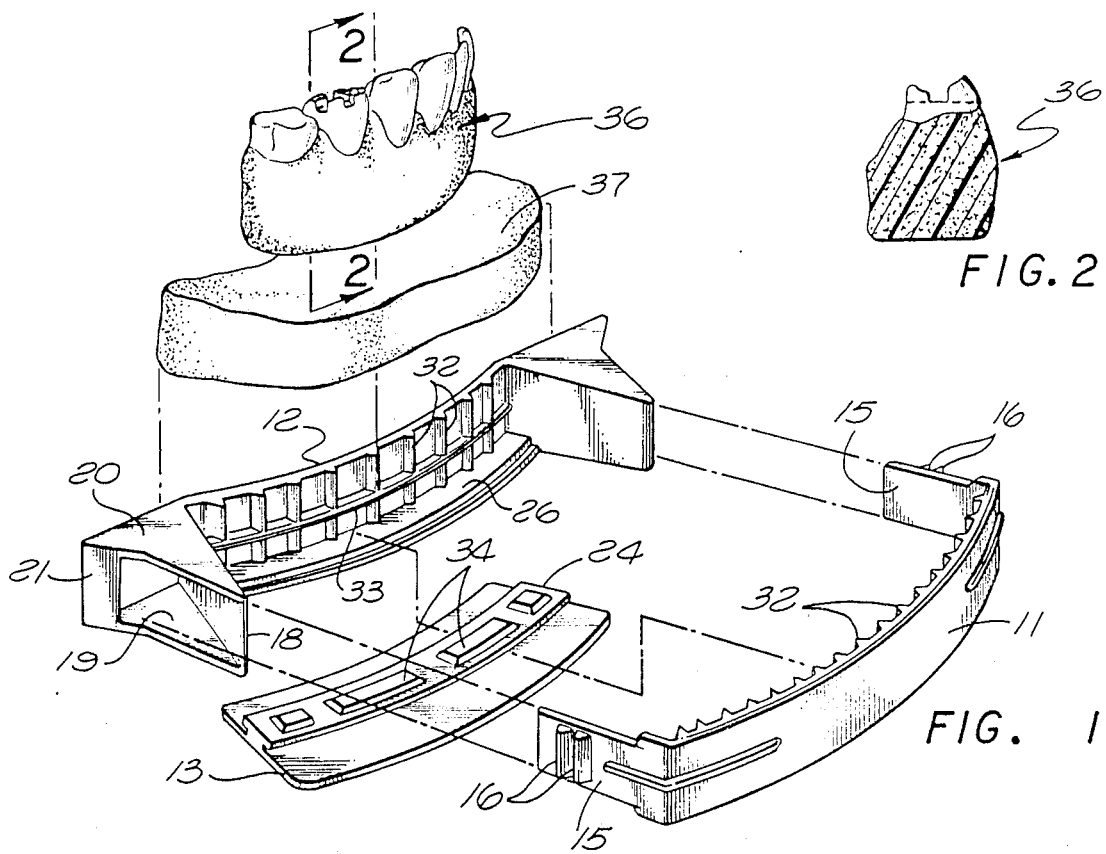
FIG. 2
FIG. 1
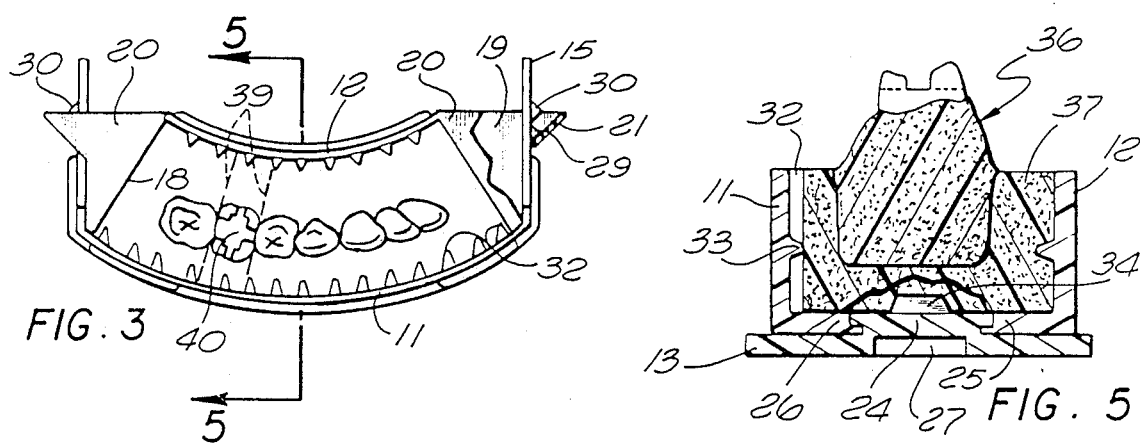
FIG. 3
FIG. 5
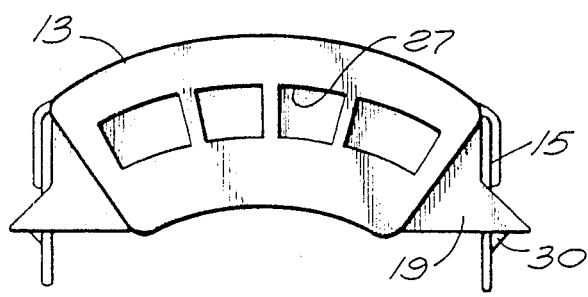
FIG. 4
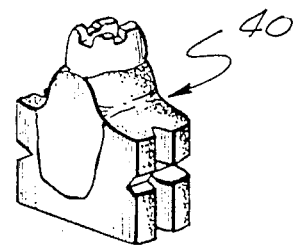
FIG. 6

DENTAL LABORATORY DIE TRAY

BACKGROUND OF THE INVENTION

This invention relates to a new and improved dental laboratory die tray, and in particular to a die tray especially suited for use in handling the refractory materials now being used in the production of dental prosthesis.

When a patient in need of crown and/or bridge dental restorative work visits a dentist, the dentist carves the affected tooth or teeth into an appropriate preparation and takes an impression of the patient's mouth. This impression is sent to a dental laboratory, along with a prescription for the dental prosthesis to be made.

Using a single pour technique the technician is able to pour the impression and the base with one mix by mixing the die stone and pouring into both the base and the impression, slightly over filling each. The technician should quickly invert the impression and position it on the filled tray. When the die stone sets, any overflow can be trimmed. The die tray allows the technician to remove the working model from the tray, separate the individual tooth or teeth to be worked on and return the working model (often in several pieces by this time) to the die tray, while maintaining the original registration of the individual teeth to the die tray and to each other.

A double pour technique can also be used in which the technician pours a working model of the patients teeth by filling the dentist's impression with die stone and allowing it to set. The portion of the model containing the affected tooth or teeth is then imbedded into a die tray filled with additional die stone.

The die tray also permits the working model to be mounted to a dental articulator. This enables the technician to develop the proper anatomy and functional occlusion of the prosthesis while still having the ability to remove the individual tooth die or dies for further work.

In the past, dental model systems were produced by plating copper or silver on the portion of the impression which was going to be restored. A cold cure acrylic resin was poured into the plated recesses and after setting, was removed and trimmed into a die. The acrylic die was re-inserted into the impression and held in position with wax. Die stone was poured into the impression, covering the die, and creating a model with a removable die.

An alternate method of making a removable die system consisted of pouring dental die stone into the impression sufficient to reproduce the tooth anatomy, grinding a flat base on the model, and drilling die pin holes into the individual teeth which are to become dies. Die pins are placed into the die stone of the teeth to be restored, and the bases of the teeth are coated with a release agent. A second pouring of a die stone encloses the pins and makes up the base of the model. The individual dies are cut from the model with a saw so that they can be removed, worked on and returned to their original position.

Because of the amount of labor involved in creating the acrylic die or the pin die system, an alternative was developed which used a die tray with an external registration to replace the die pin system. One type, sometimes called a die lock tray, has fixed sides and reinforcing ribs between the sides and an "L" shaped moveable clamp overlying a portion of the top of the tray, with a detachable hinge on one end. The moveable clamp can be removed, permitting the dies to be removed from the tray, worked on and returned to the tray without losing the original registration.

Other prior die tray systems, including one known as the Accu-Trac, consist of a tray containing an upward opening arch shaped, serrated grove to register the model, and hinged retainer clips to retain the model of the tray. The model cast and individual tooth dies are prepared in a manner similar to the methods previously described. This type of die tray positions the individual dies laterally by the upward opening groove, vertically by the retaining clips and mesially-distally by the serrated grooves.

Refractory materials are now used in the production of crowns and dentures and have been successful in producing artificial teeth with a porcelain finish of a luster and depth corresponding to that of natural teeth. While the die stone is very satisfactory in producing models from mouth impressions, the die stone has not been satisfactory in these new manufacturing processes due to the high processing temperatures involved. Therefore after the initial model is produced, a second model of a refractory material is needed for use in the high temperature casting and coating operations. The prior art die trays have not been satisfactory for these operations, and it is an object of the present invention to provide a new and improved dental laboratory die tray suitable for producing models and working on models, especially for higher operating temperatures. These and other objects, advantages, features and results will more fully appear in the course of the following description.

SUMMARY OF THE INVENTION

The die tray of the present invention provides a tray with closed sides and bottom for producing a working model in the conventional manner. Also, the die tray provides for removal and replacement of the model, removal and replacement or substitution of individual teeth in the model, and positioning of the tray in a dental articulator. Also, the die tray provides for removal of the bottom of the tray without disturbing the model, so that the model or components thereof can be worked on from the bottom as well as from the top.

The preferred embodiment of the dental laboratory die tray includes spaced side members and a bottom member with the side members having first interengaging means for releasably joining the side members to form a housing with an open top and an open bottom and defining a space for a dental model and with the bottom and side members having second interengaging means for releasably joining the bottom member to the side members for closing the open bottom of the housing. Also the first interengaging means provides for a housing closed position and a housing partially closed position, with the bottom member holdable between the side members when in the closed position and released from the side members when in the partially closed position.

BRIEF DESCRIPTION OF THE DRAWINGS

FIG. 1 is an exploded view of a dental labortory die tray incorporating the presently preferred embodiment of the invention;

FIG. 2 is a sectional view taken along the line 2—2 of FIG. 1;

FIG. 3 is a top view of the die tray of FIG. 1 in the housing closed position;

FIG. 4 is a bottom view of the die tray of FIG. 3;

FIG. 5 is a sectional view taken along the line 5—5 of FIG. 3; and

FIG. 6 is a perspective view of a model of a single die from the model of FIG. 3.

DESCRIPTION OF THE PREFERRED EMBODIMENT

The die tray as shown in the drawings comprises a side member 11, a side member 12, and a bottom member 13. In the preferred embodiment, each of these members is a plastic molding. The side members 11, 12 have interengaging means for releasably joining the members together to form a housing with an open top and an open bottom. Also, the bottom member and the two side members have interengaging means for releasably holding the bottom member to the side members for closing the open bottom of the housing. In the preferred embodiment illustrated, a tab 15 is provided at each end of the side member 11, with each tab having sawtooth projections 16. The material used in the side member 11 at the joinder of the tab to the main portion of the side member is chosen so that the tab is bendable with respect to the main portion of the side member.

The side member 12 has slots at each end for slidingly receiving the tabs 15 of the side member 11. In the preferred embodiment illustrated, a wall 18 is provided at each end of the side member 12, with the walls preferably at an oblique angle to one another. Spaced wings 19, 20 project outward from each wall 18 and are joined by a connection member 21, with the end wall, wings and connection member defining the slot for receiving the tab 15.

The preferred form for the bottom and side member interengaging means includes a ridge 24, preferably tee shaped, projecting upward from the bottom member 13, and rib engaging edges 25, 26 on the side members 11, 12, respectively. Recesses 27 may be incorporated in the lower face of the bottom member 13 to provide attachment to a dental articulator and for ease of molding. The inner surfaces of the rib engaging edges 25, 26 are stepped to mate with the tee shaped rib 24. See FIG. 5.

In the embodiment illustrated, there are two of the teeth 16 on each tab 15, shown as teeth 29 and 30 in FIG. 3. In operation, the tabs 15 of the side member 11 slide into the slots of the side member 12, with the inner ends of the connection member 21 between the teeth 29, 30. The two side members are then placed in position over the bottom member 13 and the two side members are squeezed together. This squeezing action causes the tabs to bend inward slightly toward each other, with the connection members 21 riding over the teeth 29 to the position behind the teeth 29, as shown in FIG. 3. This action also brings the rib engaging edges 25, 26 of the side members into engagement with the rib 24 of the bottom member, as shown in FIG. 5. The two side members and the bottom member are now joined together to form the die tray ready for pouring.

Preferably, means are provided on the inner faces of the side members for gripping and registering with the model to be poured in the die tray. Typically this means includes a plurality of vertical ribs 32 and one or more horizontal ribs 33. Upwardly projecting bosses 34 may be provided on the ridge 24 for improved registering with the model.

In the use of the die tray, the dentist initially carves the tooth or teeth, and then makes an impression of the mouth. This may be a partial or a complete arch cut into segments, as desired. The laboratory technician pours a model of the teeth into the dentist's impression, using conventional die stone. Using a single pour technique, the model can be poured by filling the impression and tray with die stone and placing the impression onto the die tray. Alternately, the technician can use a double pour technique and form a model by filling the impression with die stone and allowing it to set. Such a model is shown as 36 in the drawing figures. Next, this model 36 is imbedded in additional die stone, using the die tray as the mold, as seen in FIG. 5. This produces a new model comprising the original model 36 and the additional material 37. In either case, the new model is sometimes known as the working model.

The working model is removed from the die tray by squeezing the tabs 15 together and separating the side members 11, 12 apart until the connection member 21 interdigitates between teeth 29 and 30, holding the side members apart in the partially open position. The working model can be manipulated, cut, returned to and removed from the die tray as desired, with the ribs 32, 33 providing for accurate registration of the working model in the die tray.

In some laboratory work, it is desireable to remove one tooth from the model. This is accomplished with the die tray of the invention by removing the working model from the tray and cutting along the lines 39 to separate the single tooth model 40, as shown in FIGS. 3 and 6. Now the three pieces of the working model can be repositioned in the die tray, or a substitute for the single tooth model 40 can be positioned in the die tray with the other two pieces of the working model.

The die tray of the invention is particularly useful in preparing crowns, facings, inlays and onlays of the newer types of porcelain using the direct firing technique which require higher temperatures during the manufacturing process.

The model is mounted on the die tray as previously described, with the die or dies of interest removed. Then the tabs are squeezed together and the die tray is opened one tooth on the tabs 15, moving the connection members 21 from engagement with the teeth 29 to engagement with the teeth 30. This permits removal of the bottom member 13 without completely separating the side members and disturbing the model, after which the sides are again squeezed together, closing the tray. Then the refractory die material is cast by pouring the material through the central opening of the die tray into the cavity formed by the impression and the adjacent die stone.

After the refractory material has set, the resulting die can be removed and the proscribed dental prosthesis fabricated in the usual manner. By squeezing the tabs 15 together and moving the sides 11 and 12 to the partially open position, the bottom 13 can be re-inserted, permitting the die tray holding the working model and die with prosthesis attached, to be mounted on an articulator Once mounted, proper occlusion can be verified and any needed adjustments made.

We claim:

1. In a dental laboratory die tray, the combination of:
   a first side member;
   a second side member; and
   a bottom member;
   said first and second side members having first integrally formed interengaging means for releasably joining said first and second side members to form a housing with an open top and an open bottom and defining a space for a dental model, with said side members movable toward and away from each other, and with said first interengaging means including means defining a housing closed position and a housing partially closed position independently of said bottom member, with said side members separable from each other in a housing open position, and with said bottom member holdable between said side members when said side members are in said closed position and with said bottom member released from said side members when said side members are in said partially closed position, and said bottom member and said first and second side members having second integrally formed interengaging means for releasably joining said bottom member to said side members for closing said open bottom of said housing with said bottom member removable from and replaceable in between said side members when said side members are in said partially closed position.

2. In a dental laboratory die tray, the combination of:
a first side member;
a second side member; and
a bottom member;
said first and second side members having first interengaging means for releasably joining said first and second side members to form a housing with an open top and an open bottom and defining a space for a dental model; and
said bottom member and said first and second side members having second interengaging means for releasably joining said bottom member to said side members for closing said open bottom of said housing,
with one of said side members including a tab at each end and the other of said side members including a tab receiving slot at each end, with each of said tabs having teeth for selectively engaging the corresponding slot.

3. A die tray as defined in claim 2 wherein said other member has end walls oblique to each other and each forming one edge of a said slot, with the opposite edge of a slot joined to the end wall by spaced wings projecting from the end wall.

4. A die tray as defined in claim 3 wherein said second interengaging means includes an upward projecting rib carried on said bottom member and a rib engaging means on each of said side members for engaging said rib when said first interengaging means is in said housing closed position.

5. A die tray as defined in claim 4 wherein the ends of said rib abut said end walls locating said bottom member between said side members.

6. A die tray as defined in claim 4 wherein said rib is tee shaped with a wider top and a narrower base, and said rib engaging means have mating shaped inner edges.

7. In a dental laboratory die tray, the combination of:
a first side member;
a second side member; and
a bottom member,
said first and second side members having first interengaging means for releasably joining said first and second side members to form a housing with an open top and an open bottom and defining a space for a dental model; and
said bottom member and said first and second side members having second interengaging means for releasably joining said bottom member to said side members for closing said open bottom of said housing,
with said second interengaging means including an upward projecting rib carried on said bottom member and a rib engaging means on each of said side members for engaging said rib to hold said bottom member between said side members.

8. A die tray as defined in claim 7 wherein said first interengaging means includes means defining a housing closed position and a housing partially closed position, with said bottom member holdable between said side members when said side members are in said closed position and with said bottom member released from said side members when said side members are in said partially closed position, and
one of said members includes a tab at each end and the other said side members includes a tab receiving slot at each end, with each of said tabs having teeth for selectively engaging the corresponding slot.

9. A die tray as defined in claim 8 wherein the ends of said rib abut said end walls locating said bottom member between said side members, and said rib is tee shaped with a wider top and a narrower base, and said rib engaging means have mating shaped inner edges 10. A die tray as defined in claim 7 wherein said second interengaging means provides for expansion of the material in the die tray by allowing lateral movement of the said side members while at the same time restricting vertical movement of said bottom member in relation to the said side members.

11. A die tray as defined in claim 7 wherein said upward projecting rib carried on said bottom member releasably engages with material in die tray to prevent lateral motion of said bottom member should expansion of the material in said die tray move said side members laterally

* * * * *